United States Patent [19]

Prydz et al.

[11] Patent Number: 5,856,463
[45] Date of Patent: Jan. 5, 1999

[54] PSKH-1 RIBOZYMES

[76] Inventors: Hans Peter Blankenborg Prydz, Holmen vei 50 K, 0376 Oslo, Norway; Gaute Brede, Vaekeroevei 30, 0282 Oslo, Norway

[21] Appl. No.: 715,568

[22] Filed: Sep. 18, 1996

[30] Foreign Application Priority Data

Sep. 18, 1995 [NO] Norway ................................ 953680

[51] Int. Cl.⁶ .............................. C07H 21/04; C12Q 1/68
[52] U.S. Cl. ....................... 536/24.5; 536/23.1; 536/23.2; 435/6; 435/91.31; 435/375
[58] Field of Search .......................... 435/6, 91.31, 199, 435/375; 514/44; 536/24.5; 935/33

[56] References Cited

U.S. PATENT DOCUMENTS

| | | | |
|---|---|---|---|
| 5,144,019 | 9/1992 | Rossi et al. | 536/23.1 |
| 5,246,921 | 9/1993 | Reddy et al. | 514/44 |
| 5,272,262 | 12/1993 | Rossi et al. | 536/23.2 |
| 5,436,330 | 7/1995 | Taira et al. | 536/23.2 |
| 5,441,880 | 8/1995 | Beach et al. | 435/193 |
| 5,443,962 | 8/1995 | Draetta et al. | 435/29 |
| 5,459,127 | 10/1995 | Felgner et al. | 514/7 |
| 5,496,698 | 3/1996 | Draper et al. | 435/6 |
| 5,527,895 | 6/1996 | Hampel et al. | 536/23.2 |

FOREIGN PATENT DOCUMENTS

WO 9524202  9/1995  WIPO .

OTHER PUBLICATIONS

Christoffersen et al. Ribozymes as Human Therapeutic Agents. J. Med. Chem. 38(12): 2023–2037, Jun. 1995.
Gewirtz et al. Facilitating Oligonucleotide Delivery: Helping Antisense Deliver on its Promise. Proc. Natl. Acad. Sci. USA 93 3161–3163, Apr. 1996.
Gura. Antisense has Growing Pains. Science 270: 575–577, Oct. 1995.
Stull et al. Antigens, Ribozyme and Aptamer Nucleic Acid Drugs: Progress and Prospects. 12(4): 465–482, Apr. 1995.
Larsen et al., Hum. Mol. Gen. 2(10):1589–1595 (1995).
Hanks, Proc. Natl. Acad. Sci. USA 84:388–392 (1987).
Kim et al., Proc. Natl. Acad. Sci. USA 84:8788–8792 (1987).
Haseloff et al., Nature 334:585–591 (1988).
Cech, JAMA 260(20):3030–3034 (1988).
Jefferies et al., Nucl. Acad. Res. 1989, 17, 1371.
Cech et al., Nature 372:39–40 (1994).
Uhlenbeck, Nature 328:596–600 (1987).
Forster et al., Cell 50:9–16 (1987).
Pley et al., Nature 372:68–74 (1994).
Tuschl et al., Science 266:785–789 (1994).
Pyle, Science 261:709–714 (1993).
Hampel et al., 28 Biochemistry 4929, 1989.
Hampel et al., 18 Nucleic Acid research 299, 1990.
Felgner et al., Proc. Natl. Acad. Sci. USA 84:7413–7417 (1987).
Pachuk et al., Proc. Annu. Meet Am Assoc. Cancer Res. 34:A2313 (1993) (Abstract Only).
Leopold et al., Blood (United States)85:2162–70 (1995) (Abstract Only).
Vertosick et al., J. Neurooncol (Netherlands) 19(2):97–103 (1994) (Abstract Only).
Baier et al., Mol. Immunol. 31(12):923–32 (1994) (Abstract Only).

*Primary Examiner*—John L. LeGuyader
*Assistant Examiner*—Thomas G. Larsen
*Attorney, Agent, or Firm*—Lerner, David, Littenberg, Krumholz & Mentlik

[57] ABSTRACT

Disclosed is a purified full-length cDNA molecule encoding putative serine kinase enzyme (PSKH-1), and the expression of the cDNA in a recombinant host cell to produce substantially purified PSKH-1, per se. Inactivation of PSKH-1 pre-mRNA or PSKH-1 mRNA halts DNA synthesis and cell division. Also disclosed are ribozymes capable of cleaving PSKH-1 pre-mRNA or mRNA and thus deactivating PSKH-1 translation. Ribozymes of the hammerhead and hairpin motifs, and various compositions containing same, are also disclosed. The ribozymes compositions are used in the treatment of mammalian patients suffering from diseases or medical conditions characterized by abnormal cell proliferation or growth such as cancer and various non-malignant diseases or medical conditions such as autoimmune diseases, allograft rejection and atherosclerosis.

9 Claims, 5 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 424 amino acids
      ( B ) TYPE: amino acid
      ( D ) TOPOLOGY: linear ( x i ) SEQUENCE DESCRIPTION: SEQ ID NO:1:

```
Met Gly Cys Gly Thr Ser Lys Val Leu Pro Glu Pro Pro Lys Asp Val
 1               5                  10                  15
Gln Leu Asp Leu Val Lys Lys Val Glu Pro Phe Ser Gly Thr Lys Ser
            20                  25                  30
Asp Val Tyr Lys His Phe Ile Thr Glu Val Asp Ser Val Gly Pro Val
             35                  40                  45
Lys Ala Gly Phe Pro Ala Ala Ser Gln Tyr Ala His Pro Cys Pro Gly
         50                  55                  60
Pro Pro Thr Ala Gly His Thr Glu Pro Pro Ser Glu Pro Pro Arg Arg
 65                  70                  75                  80
Ala Arg Val Ala Lys Tyr Arg Ala Lys Phe Asp Pro Arg Val Thr Ala
                 85                  90                  95
Lys Tyr Asp Ile Lys Glu Ile Ile Gly Arg Gly Ser Phe Ser Arg Val
                100                 105                 110
Val Arg Val Glu His Arg Ala Thr Arg Gln Pro Tyr Ala Ile Lys Met
             115                 120                 125
Ile Glu Thr Lys Tyr Arg Glu Gly Arg Glu Val Cys Glu Ser Glu Leu
         130                 135                 140
Arg Val Leu Arg Arg Val Arg His Ala Asn Ile Ile Gln Leu Val Glu
145                 150                 155                 160
Val Phe Glu Thr Gln Glu Arg Val Tyr Met Val Met Glu Leu Ala Thr
                165                 170                 175
Gly Gly Glu Leu Phe Asp Arg Ile Ile Ala Lys Gly Ser Phe Thr Glu
            180                 185                 190
Arg Asp Ala Thr Arg Val Leu Gln Met Val Leu Asp Gly Val Arg Tyr
         195                 200                 205
Leu His Ala Leu Gly Ile Thr His Arg Asp Leu Lys Pro Glu Asn Leu
    210                 215                 220
Leu Tyr Tyr His Pro Gly Thr Asp Ser Lys Ile Ile Ile Thr Asp Phe
225                 230                 235                 240
Gly Leu Ala Ser Ala Arg Lys Lys Gly Asp Asp Cys Leu Met Lys Thr
                245                 250                 255
Thr Cys Gly Thr Pro Glu Tyr Ile Ala Pro Glu Val Leu Val Arg Lys
            260                 265                 270
Pro Tyr Thr Asn Ser Val Asp Met Trp Ala Leu Gly Val Ile Ala Tyr
         275                 280                 285
Ile Leu Leu Ser Gly Thr Met Pro Phe Glu Asp Asp Asn Arg Thr Arg
    290                 295                 300
Leu Tyr Arg Gln Ile Leu Arg Gly Lys Tyr Ser Tyr Ser Gly Glu Pro
305                 310                 315                 320
Trp Pro Ser Val Ser Asn Leu Ala Lys Asp Phe Ile Asp Arg Leu Leu
                325                 330                 335
```

```
            Thr  Val  Asp  Pro  Gly  Ala  Arg  Met  Thr  Ala  Leu  Gln  Ala  Leu  Arg  His
                      340                      345                          350

Pro  Trp  Val  Val  Ser  Met  Ala  Ala  Ser  Ser  Ser  Met  Lys  Asn  Leu  His
                           355                 360                     365

Arg  Ser  Ile  Ser  Gln  Asn  Leu  Leu  Lys  Arg  Ala  Ser  Ser  Arg  Cys  Gln
                      370                      375                      380

Ser  Thr  Lys  Ser  Ala  Gln  Ser  Thr  Arg  Ser  Ser  Arg  Ser  Thr  Arg  Ser
            385                      390                          395                      400

Asn  Lys  Ser  Arg  Arg  Val  Arg  Glu  Arg  Glu  Leu  Arg  Glu  Leu  Asn  Leu
                                405                      410                          415

Arg  Tyr  Gln  Gln  Gln  Tyr  Asn  Gly
                           420
```

( 2 ) INFORMATION FOR SEQ ID NO:2:

( i ) SEQUENCE CHARACTERISTICS:
        ( A ) LENGTH: 3471 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CGAAGAGCCC  GCCGCCGCG   CGAGGTGTAG  ACGGGGCACT  GCCTTCAGAG  CAGGTCCTGC      60

CAGCCTCGCT  GAAGAGGATG  CCCTCGTGTC  CGTGATGGGC  TGTGGGACAA  GCAAGGTCCT     120

TCCCGAGCCA  CCCAAGGATG  TCCAGCTGGA  TCTGGTCAAG  AAGGTGGAGC  CCTTCAGTGG     180

CACTAAGAGT  GACGTGTACA  AGCACTTCAT  CACAGAGGTG  GACAGTGTTG  GCCCTGTCAA     240

AGCCGGGTTC  CCAGCAGCAA  GTCAGTATGC  ACACCCCTGC  CCCGGTCCCC  CGACTGCTGG     300

CCACACGGAG  CCTCCCTCAG  AACCACCACG  CAGGGCCAGG  GTAGCTAAGT  ACAGGGCCAA     360

GTTTGACCCA  CGTGTTACAG  CTAAGTATGA  CATCAAGGAA  ATAATTGGCC  GAGGCAGCTT     420

CAGCCGAGTG  GTACGTGTAG  AGCACCGGGC  AACCCGGCAG  CCGTATGCCA  TCAAGATGAT     480

TGAGACCAAG  TACCGGGAGG  GGCGGGAGGT  GTGTGAGTCG  GAGCTGCGTG  TGCTGCGTCG     540

GGTGCGTCAT  GCCAACATCA  TCCAGCTGGT  GGAGGTGTTC  GAGACACAGG  AGCGGGTGTA     600

CATGGTGATG  GAGCTGGCCA  CTGGTGGAGA  GCTCTTTGAC  CGCATCATTG  CCAAGGGCTC     660

CTTCACCGAG  CGTGACGCCA  CGCGGGTGCT  GCAGATGGTG  CTGGATGGCG  TCCGGTATCT     720

GCATGCACTG  GGCATCACAC  ACCGAGACCT  CAAACCTGAG  AATCTGCTCT  ACTACCATCC     780

GGGCACTGAC  TCCAAGATCA  TCATCACCGA  CTTCGGCCTG  GCCAGTGCTC  GCAAGAAGGG     840

TGATGACTGC  TTGATGAAGA  CCACCTGTGG  CACGCCTGAG  TACATTGCCC  AGAAGTCCT     900

GGTCCGCAAG  CCATACACCA  ACTCAGTGGA  CATGTGGGCG  CTGGGCGTCA  TTGCCTACAT     960

CCTACTCAGT  GGCACCATGC  CGTTTGAGGA  TGACAACCGT  ACCCGGCTGT  ACCGGCAGAT    1020

CCTCAGGGGC  AAGTACAGTT  ACTCTGGGGA  GCCCTGGCCT  AGTGTGTCCA  ACCTGGCCAA    1080

GGACTTCATT  GACCGCCTGC  TGACAGTGGA  CCCTGGAGCC  CGTATGACTG  CACTGCAGGC    1140

CCTGAGGCAC  CCGTGGGTGG  TGAGCATGGC  TGCCTCTTCA  TCCATGAAGA  ACCTGCACCG    1200

CTCCATATCC  CAGAACCTCC  TTAAACGTGC  CTCCTCGCGC  TGCCAGAGCA  CCAAATCTGC    1260

CCAGTCCACG  CGTTCCAGCC  GCTCCACACG  CTCCAATAAG  TCACGCCGTG  TGCGGGAACG    1320

GGAGCTGCGG  GAGCTCAACC  TGCGCTACCA  GCAGCAATAC  AATGGCTGAG  CCGAATGGCT    1380

GTGCACACAT  GCAGCACGAC  CCAGCCTGGC  CACACACTGT  GGTGCCATCT  GGGTCCGATG    1440

CCCTCTCTGG  AGATAGGCCT  ATGTGGCCCA  CAGTAGGTGA  AGAATGTCTG  GCTCCAGCCC    1500

TTTCTCTGTC  GGTTCACCAG  CCCCTGTCCT  CACCATGGGC  CTGGGCCAGG  TGTGACAGAG    1560
```

| | | | | | | |
|---|---|---|---|---|---|---|
| TAGAGGTAGC | ACAGGGGGCT | GTCCTCACCA | TGGGCCTGGG | CCAGGTGTGA | CAGAGTAGAG | 1620 |
| GTAGCACAGG | GGGCTGTGAC | TCCCCCTGAA | CTGGGAGCCT | GGCCTGGCAG | TGATACCCCT | 1680 |
| CTTGGTGGGC | AGCTGCTCTG | GTGGAGTTGG | GAAGGGATAG | GACCTGGCCT | TCACTGTCTC | 1740 |
| CCTTGCCCTT | TGACTTTTCC | CCAATCAAAG | GGAACTGCAG | TGCTGGGTGG | AGTGTCCTGT | 1800 |
| CGCCTCAGGA | CCCTTTGGGA | CAGTTACTTC | TGGGACCCCC | TTTCCTCCAC | AGAGCCCTTC | 1860 |
| TCCCTCCTTT | CACACATTCC | CATGCATCCT | GATCCTTAAG | ATTATGCTCC | AGTGGGAGAC | 1920 |
| CCTGGTAGGC | ACAAAGCTTG | TGCCTTGACT | GGACCCGTAG | CCCCTGGCTA | GGTCGAAACA | 1980 |
| GCCCTCCACC | TCCCAGCCAA | GATCTGTCTT | CCTTCATGGT | GCCTCCAGGG | AGCCTTCCTG | 2040 |
| GTCCAGGAC | CTCTGGTGGA | GGGCCATGGC | GTGGACCTTC | ACCCTTCTGG | ACTGTGTGGC | 2100 |
| CATGCTGGTC | ATCGGCTTGC | CCAGGCTCCA | GCCTCTCCAG | ATTCTGAGGG | GTCTCAGCCC | 2160 |
| ACCGCCCTTG | GTGCCTTCTT | TGTAGAGCCC | ACCGCTACCT | CCCTCTCCCC | GTTGGATGTC | 2220 |
| CATTCCATTC | CCCAGGTGCC | TCCTTCCCAA | CTGGGGGTGG | TTAAAGGGAC | GCCCACTGCT | 2280 |
| GCTACCTGGG | GAATGGGGCA | CCTGGGGCCC | AAGGCAGAGG | GAAGGGGGTC | CTCCCGATTA | 2340 |
| GGGTCGAGTG | TCAGCCTGGG | TTCTATCCTT | TGGTGCAGCC | CCATTGCCTT | TTCCCTTCAG | 2400 |
| GCTCTGTTGC | TCCCTCCTCT | GCAGCTGCAC | GAAGGCGCCA | TCTGGTGTCT | GCATGGGTGT | 2460 |
| TGGCAGCCTG | GGAGTGATCA | CTGCACGCCC | ATCCTCCACA | CCTGCCCATC | GTGCACACCC | 2520 |
| ACCCATGGTG | CACACCTGTA | GTCCTCCATG | AGGACATGGG | AAGGTAGGAG | TTGCCGCCCT | 2580 |
| GGGGGAGGGT | CCCGGGCTGC | TCACCTCTCC | CCTTCTGCTG | AGCTTCTGCG | CACCCCTCCC | 2640 |
| TGGAACTTAG | CCATACTGTG | TGACCTGCCT | CTGAAACCAG | GGTGCCAGGG | GCACTGCCTT | 2700 |
| CTCACAGCTG | GCCTTGCCCC | GTCCACCCTG | TGCTGCTTCC | CTTCACAGCA | TTAACCTTCC | 2760 |
| AGTCTGGGTC | CCACTGAGCC | TCAAGCTGGA | AGGAGCCCCT | GCGGGAGGTG | GGTGGGGTTG | 2820 |
| GGTGGCTGCT | TTCCCAGAGG | CCTGACGCCA | GAACCATCCC | CATTTCTTTT | GTGGTATCTC | 2880 |
| CCCCTACCAC | AAACCAGGCT | GGAACCCAAG | CCCCTTCCTC | CACAGCTGCC | TTCAGTGGGT | 2940 |
| AGAATGGGGC | CAGGGCCCAG | CTTTGGCCTT | AGCTTGACGG | CAGGGCCCCT | GCCATTGCAC | 3000 |
| GAGGGTTTGG | TTCCCACTCA | GCTTCTCCGG | TCGGCAGCCT | GGGCCAGGCC | CTTTTCCTGC | 3060 |
| ATGTGCCACC | TCCAGTGGGA | AACAAAACTA | AAGAGACCAC | TCTGTGCCAA | GTCGACTATG | 3120 |
| CCTTAGACAC | ATCCTCCTAC | CGTCCCCAAT | GCCCTGGGC | AGGAGGCAGT | GGAGAACCAA | 3180 |
| GCCCCATGGC | CTCAGAATTT | CCCCCCAGTT | CCCCAAGTGT | CTCTGGGGAC | CTGAAGCCCT | 3240 |
| GGGGCTTACG | TTCTCTCTTG | CCCAGGGTGG | CCTGGTCCTG | AGGGCAGGAC | AGGGGGTTTG | 3300 |
| CAGATGTGGG | CCTTTGATAG | ACCCACTTGG | GCCTTCATGC | CATGGCCTGT | GGATGGAGAA | 3360 |
| TGTGCAGTTA | TTTATTATGC | GTATTCAGTT | TGTAAACGTA | TCCTCTGTAT | TCAGTAAACA | 3420 |
| GGCTGCCTCT | CCAGGGAGGG | CTGCCATTCA | TTCCAACAAA | AAAAAAAAA | A | 3471 |

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | |
|---|---|---|---|
| ACAGCUGCUG | AUGAGGCCGU | UAGGCCGAAA | CAUCC | 35 |

( 2 ) INFORMATION FOR SEQ ID NO:4:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GGAUGUCCAG CUGG    14

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 8
        ( D ) OTHER INFORMATION: /note= "N at this position
            represents 2,3 or 4 of any base (A,C,G,U)"

( i x ) FEATURE:
        ( A ) NAME/KEY: misc_feature
        ( B ) LOCATION: 13
        ( D ) OTHER INFORMATION: /note= "N at this position
            represents 2,3 or 4 nucleotides complementary to
            nucleotides in position 8 to allow for the ( x i ) SEQUENCE DESCRIPTION: SEQ ID NO:5:

CUGANGANNN NNNGAAA    17

( 2 ) INFORMATION FOR SEQ ID NO:6:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: both ( x i ) SEQUENCE DESCRIPTION: SEQ ID NO:6:

CAGCUGAGAA UCCUACCAGA GAAACACACG UUGUGGUAUA UUACCUGGUA    50

( 2 ) INFORMATION FOR SEQ ID NO:7:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AGGAUGUCCA GCUG    14

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTGTGCATAC TGACTTGCTG    20

( 2 ) INFORMATION FOR SEQ ID NO:9:

( i ) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

TCCACCTCTG TGATGAAGTG                                                                                    20

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:10:

CACGAATTCA CTATCGATTC TGGAACCTTC AGAGG                                                                   35

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

TCCACCTCTG TGATGAAGTG                                                                                    20

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:12:

CTGGTTCGGC CCACCTCTGA AGGTTCCAGA ATCGATAG                                                                38

(2) INFORMATION FOR SEQ ID NO:13:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:13:

Asn Lys Ser Arg Arg Val Arg Glu Arg Glu Leu Arg Glu Leu Asn Leu
         1               5                  10                  15

Arg Tyr Gln Gln
                    20

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:14:

ACAGCUGCUA AUGAGGCCGU UAGGCCGAAA CAUCC                                                                   35

PSKH-1 RIBOZYMES

FIELD OF THE INVENTION

The invention relates to the field of catalytic RNAs or ribozymes, and their use to treat diseases and other medical conditions characterized by uncontrolled cell growth.

BACKGROUND OF THE INVENTION

In recent years, some progress has been made in the elucidation of cellular events leading to the development of progression of diseases and other medical conditions characterized by abnormal cell growth. For instance, a great amount of research has centered on the identification of genes which are altered or mutated in cancer relative to normal cells. Nonetheless, current cancer treatment modalities are still inadequate in one or more respects. In cancer patients, the prominent immune depression in response to chemotherapy has been widely confirmed. Accordingly, immunotherapy and immunochemotherapy have drawn much attention as adjuvants to existing cancer treatments. Immunotherapy has been reported as not only restoring or potentiating the specific immune responses against cancer, but also improving the general immunological functions of the patient. However, the immunomodulators used in such therapies tend to act in a non-specific manner against cancer cells and also exert direct cytocidal affects against neoplastic cells and behave in a manner more akin to chemotherapeutic agents.

A variety of non-malignant disease states are also characterized by abnormal cell growth. Allograft rejection and autoimmune diseases, for example, involve immune responses characterized by undesirable proliferative bursts of B-lymphocytes or T-lymphocytes. Current treatment modalities for these diseases and medical conditions typically involve immunosuppresive protocols. In the case of allograft rejection, illustrative protocols have featured the administration of drugs such as azathioprine, cyclosporine, and corticosteroids, all of which cause toxic side-effects to non-lymphoid tissues. The development of pan-T-lymphocyte-specific monoclonal antibodies was purported to be an important refinement in therapy on the basis that antibodies targeted only the T-lymphocytes. However, this therapy has proven to be disadvantageous in that it also destroys T-lymphocytes required for normal immune surveillance.

The phenotype common to cancers and the aforementioned non-malignant diseases is abnormal cell growth. The life cycle of a cell is traditionally divided into four phases, G1 (Gap 1), S (DNA synthesis), G2 (Gap 2), and M (mitosis). In the mitosis phase, chromosomes condense and become visible as discrete bodies. The two centrosomes of the cell move apart to opposite sides of the nucleus, and arrays of microtubules grow from the centrosomes to form a mitotic spindle. The centrosomes thus define the anchoring points for the microtubuli which in turn direct the chromosomes to the proper place in the cell. Some of these microtubules become attached to the kinetochores of the chromosomes. The attached chromosomes become aligned on the metaphase plate, anaphase begins and the chromosomes start moving toward the poles and the poles move apart from each other. Cytokinesis then occurs, wherein the cell pinches and ultimately becomes two G1 phase daughter cells. G1 are not synthesizing DNA, but active in other replication-type activities in order to provide the two daughter cells with the appropriate organelles. G1 cells then proceed into the S phase where the chromosomal DNA of the cell replicates to produce double DNA content. At the boundary of the S and the G2 phases, the replication machinery signals that DNA replication is complete. The cell then enters the G2 phase and prepares for mitosis. Thus, cells in the G2 phase have double DNA content. It is critical that cell division proceeds in an orderly manner such that each daughter cell receives a correct and complete set of chromosomes. Most adult, differentiated non-dividing cells are considered to be in a non-cycling state termed $G_0$.

If the mechanisms that underlie cell division could be disarmed or inactivated, procedures and perhaps even pharmacologic agents could be developed in an attempt to control or inhibit the growth of unwanted, diseased cells in a wide variety of cancers and non-malignant diseases characterized by abnormal cell growth. It goes without saying that such discoveries would be of pioneering proportions in clinical medicine.

SUMMARY OF THE INVENTION

Applicant has now succeeded in isolating and purifying a full-length cDNA molecule encoding a putative serine kinase enzyme (PSKH-1). The substrate for this enzyme and the reaction conditions in vivo still remain unknown. However, Applicant has expressed PSKH-1 cDNA in recombinant host cells to prepare substantially purified PSKH-1 protein, and has raised anti-PSKH-1 antibodies. Intrigued by the results of experiments that pinpointed the cellular localization of PSKH-1 in or on the centrosomes, Applicant conducted further experiments to determine the fate of the cell life cycle if this enzyme were inactivated. Applicant has surprisingly and unexpectedly discovered that disarming or inactivating the expression of PSKH-1 in cells arrests or halts DNA synthesis and cell division.

One aspect of the present invention is directed to an isolated and purified cDNA molecule encoding full-length PSKH-1 protein, as well as PSKH-1, per se. Also provided are expression constructs, vectors and host cells containing PSKH-1 cDNA, and methods for preparing substantially purified PSKH-1 via recombinant techniques.

Another aspect of the present invention is directed to ribozymes or enzymatically active RNA molecules, capable of cleaving PSKH-1 pre-mRNA or PSKH-1 mRNA so as to prevent PSKH-1 expression in vivo. Preferred ribozymes are of the hammerhead or the hairpin motifs. The ribozymes are formulated into compositions useful for treating mammalian patients suffering from diseases or medical conditions characterized by abnormal or uncontrolled cell proliferation or growth. Representative compositions include slow-release devices such as micropumps, biodegradable vehicles, alginates having defined pore sizes, and target cell-specific liposomes. In a preferred embodiment wherein the composition contains a hammerhead ribozyme that is sufficiently hydrophobic so as to be internalized by the target cells on its own, i.e., without a liposome-type vehicle, the composition is provided simply in the form of an aqueous solution in a slow-release device.

A further aspect of the present invention is directed to the use of the ribozyme compositions in methods for treating mammalian patients suffering from such diseases or medical conditions such as cancers and malignancies, as well as a variety of non-malignant diseases characterized by abnormal or uncontrolled cell proliferation or growth such as autoimmune diseases, allograft rejection, and atherosclerosis.

BRIEF DESCRIPTION OF THE DRAWINGS

The file of this patent contains at least one drawing executed in color. Copies of this patent with colored drawings will be provided by the Patent and Trademark Office upon request and payment of the necessary fee.

DETAILED DESCRIPTION OF THE PREFERRED EMBODIMENT

Figure 1:
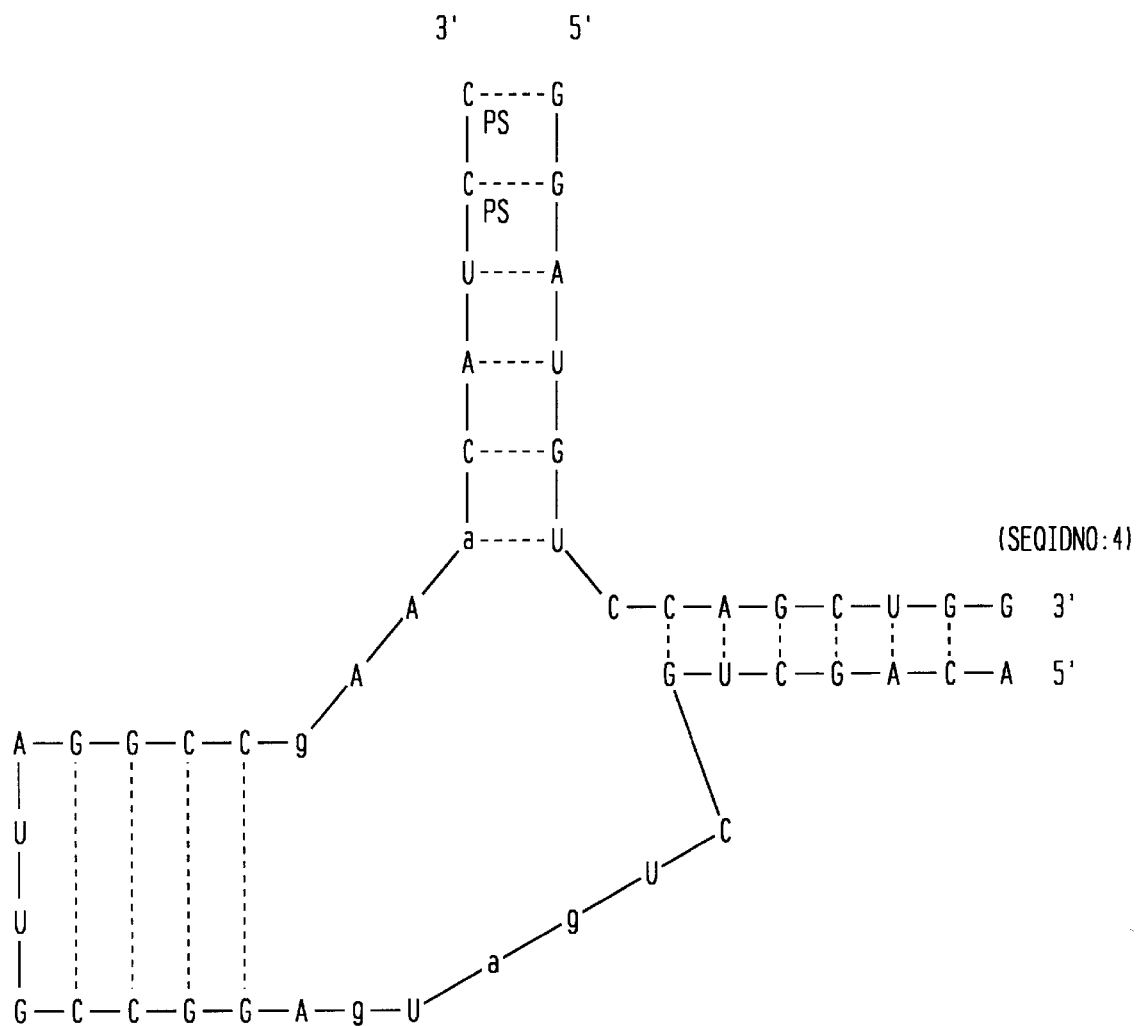
FIG. 1 is a schematic diagram of the secondary structure of a complex between a preferred hammerhead ribozyme (denoted as SEQ ID NO:3) in accordance with the present invention and a specific sequence of PSKH-1 mRNA (denoted as SEQ ID NO:4), (bases in bold) wherein the (- - -) represent Watson-Crick hydrogen bonding and "PS" indicates phosphothioate bonds.

The nucleotide sequence of the full-length PSKH-1 cDNA, i.e., including the 5' untranslated sequence (nucleotides 1–94), protein-encoding sequence, and 3' untranslated sequence (2084 nucleotides in length), and its deduced amino acid sequence, are set forth below in Table I as SEQ ID NOS:1 and 2, respectively.

TABLE I

| CGAAGAGCCCGCCGCCCGCGCGAGGTGTAGACGGGGCACTGCCTTCAGAGCAGG | | | | | | | | | | | | 54 |
|---|---|---|---|---|---|---|---|---|---|---|---|---|
| TCCTGCCAGCCTCGCTGAAGAGGATGCCCTCGTGTCCGTG | | | | | | | | ATG | GGC | TGT | | 103 |
| | | | | | | | | Met | Gly | Cys | | |
| GGG | ACA | AGC | AAG | GTC | CTT | CCC | GAG | CCA | CCC | AAG | GAT | GTC | 142 |
| Gly | Thr | Ser | Lys | Val | Leu | Pro | Glu | Pro | Pro | Lys | Asp | Val | |
| CAG | CTG | GAT | CTG | GTC | AAG | AAG | GTG | GAG | CCC | TTC | AGT | GGC | 181 |
| Gln | Leu | Asp | Leu | Val | Lys | Lys | Val | Glu | Pro | Phe | Ser | Gly | |
| ACT | AAG | AGT | GAC | GTG | TAC | AAG | CAC | TTC | ATC | ACA | GAG | GTG | 220 |
| Thr | Lys | Ser | Asp | Val | Tyr | Lys | His | Phe | Ile | Thr | Glu | Val | |
| GAC | AGT | GTT | GGC | CCT | GTC | AAA | GCC | GGG | TTC | CCA | GCA | GCA | 259 |
| Asp | Ser | Val | Gly | Pro | Val | Lys | Ala | Gly | Phe | Pro | Ala | AlA | |
| AGT | CAG | TAT | GCA | CAC | CCC | TGC | CCC | GGT | CCC | CCG | ACT | GCT | 298 |
| Ser | Gln | Tyr | Ala | His | Pro | Cys | Pro | Gly | Pro | Pro | Thr | AlA | |
| GGC | CAC | ACG | GAG | CCT | CCC | TCA | GAA | CCA | CCA | CGC | AGG | GCC | 337 |
| Gly | His | Thr | Glu | Pro | Pro | Ser | Glu | Pro | Pro | Arg | Arg | Ala | |
| AGG | GTA | GCT | AAG | TAC | AGG | GCC | AAG | TTT | GAC | CCA | CGT | GTT | 376 |
| Arg | Val | Ala | Lys | Tyr | Arg | Ala | Lys | Phe | Asp | Pro | Arg | Val | |
| ACA | GCT | AAG | TAT | GAC | ATC | AAG | GAA | ATA | ATT | GGC | CGA | GGC | 415 |
| Thr | Ala | Lys | Tyr | Asp | Ile | Lys | Glu | Ile | Ile | Gly | Arg | Gly | |
| AGC | TTC | AGC | CGA | GTG | GTA | CGT | GTA | GAG | CAC | CGG | GCA | ACC | 454 |
| Ser | Phe | Ser | Arg | Val | Val | Arg | Val | Glu | His | Arg | Ala | Thr | |
| CGG | CAG | CCG | TAT | GCC | ATC | AAG | ATG | ATT | GAG | ACC | AAG | TAC | 493 |
| Arg | Gln | Pro | Tyr | Ala | Ile | Lys | Met | Ile | Glu | Thr | Lys | Tyr | |
| CGG | GAG | GGG | CGG | GAG | GTG | TGT | GAG | TCG | GAG | CTG | CGT | GTG | 532 |
| Arg | Glu | Gly | Arg | Glu | Val | Cys | Glu | Ser | Glu | Leu | Arg | Val | |
| CTG | CGT | CGG | GTG | CGT | CAT | GCC | AAC | ATC | ATC | CAG | CTG | GTG | 571 |
| Leu | Arg | Arg | Val | Arg | His | Ala | Asn | Ile | Ile | Gln | Leu | Val | |
| GAG | GTG | TTC | GAG | ACA | CAG | GAG | CGG | GTG | TAC | ATG | GTG | ATG | 610 |
| Glu | Val | Phe | Glu | Thr | Gln | Glu | Arg | Val | Tyr | Met | Val | Met | |
| GAG | CTG | GCC | ACT | GGT | GGA | GAG | CTC | TTT | GAC | CGC | ATC | ATT | 649 |
| Glu | Leu | Ala | Thr | Gly | Gly | Glu | Leu | Phe | Asp | Arg | Ile | Ile | |
| GCC | AAG | GGC | TCC | TTC | ACC | GAG | CGT | GAC | GCC | ACG | CGG | GTG | 688 |
| Ala | Lys | Gly | Ser | Phe | Thr | Glu | Arg | Asp | Ala | Thr | Arg | Val | |
| CTG | CAG | ATG | GTG | CTG | GAT | GGC | GTC | CGG | TAT | CTG | CAT | GCA | 727 |
| Leu | Gln | Met | Val | Leu | Asp | Gly | Val | Arg | Tyr | Leu | His | Ala | |
| CTG | GGC | ATC | ACA | CAC | CGA | GAC | CTC | AAA | CCT | GAG | AAT | CTG | 766 |
| Leu | Gly | Ile | Thr | His | Arg | Asp | Leu | Lys | Pro | Glu | Asn | Leu | |

TABLE I-continued

| | | | | | | | | | | | | | |
|---|---|---|---|---|---|---|---|---|---|---|---|---|---|
| CTC | TAC | TAC | CAT | CCG | GGC | ACT | GAC | TCC | AAG | ATC | ATC | ATC | 805 |
| Leu | Tyr | Tyr | His | Pro | Gly | Thr | Asp | Ser | Lys | Ile | Ile | Ile | |
| ACC | GAC | TTC | GGC | CTG | GCC | AGT | GCT | CGC | AAG | AAG | GGT | GAT | 844 |
| Thr | Asp | Phe | Gly | Leu | Ala | Ser | Ala | Arg | Lys | Lys | Gly | Asp | |
| GAC | TGC | TTG | ATG | AAG | ACC | ACC | TGT | GGC | ACG | CCT | GAG | TAC | 883 |
| Asp | Cys | Leu | Met | Lys | Thr | Thr | Cys | Gly | Thr | Pro | Glu | Tyr | |
| ATT | GCC | CCA | GAA | GTC | CTG | GTC | CGC | AAG | CCA | TAC | ACC | AAC | 922 |
| Ile | Ala | Pro | Glu | Val | Leu | Val | Arg | Lys | Pro | Tyr | Thr | Asn | |
| TCA | GTG | GAC | ATG | TGG | GCG | CTG | GGC | GTC | ATT | GCC | TAC | ATC | 961 |
| Ser | Val | Asp | Met | Trp | Ala | Leu | Gly | Val | Ile | Ala | Tyr | Ile | |
| CTA | CTC | AGT | GGC | ACC | ATG | CCG | TTT | GAG | GAT | GAC | AAC | CGT | 1000 |
| Leu | Leu | Ser | Gly | Thr | Met | Pro | Phe | Glu | Asp | Asp | Asn | Arg | |
| ACC | CGG | CTG | TAC | CGG | CAG | ATC | CTC | AGG | GGC | AAG | TAC | AGT | 1039 |
| Thr | Arg | Leu | Tyr | Arg | Gln | Ile | Leu | Arg | Gly | Lys | Tyr | Ser | |
| TAC | TCT | GGG | GAG | CCC | TGG | CCT | AGT | GTG | TCC | AAC | CTG | GCC | 1078 |
| Tyr | Ser | Gly | Glu | Pro | Trp | Pro | Ser | Val | Ser | Asn | Leu | Ala | |
| AAG | GAC | TTC | ATT | GAC | CGC | CTG | CTG | ACA | GTG | GAC | CCT | GGA | 1117 |
| Lys | Asp | Phe | Ile | Asp | Arg | Leu | Leu | Thr | Val | Asp | Pro | Gly | |
| GCC | CGT | ATG | ACT | GCA | CTG | CAG | GCC | CTG | AGG | CAC | CCG | TGG | 1156 |
| Ala | Arg | Met | Thr | Ala | Leu | Gln | Ala | Leu | Arg | His | Pro | Trp | |
| GTG | GTG | AGC | ATG | GCT | GCC | TCT | TCA | TCC | ATG | AAG | AAC | CTG | 1195 |
| Val | Val | Ser | Met | Ala | Ala | Ser | ser | Ser | Met | Lys | Asn | Leu | |
| CAC | CGC | TCC | ATA | TCC | CAG | AAC | CTC | CTT | AAA | CGT | GCC | TCC | 1234 |
| His | Arg | Ser | Ile | Ser | Gln | Asn | Leu | Leu | Lys | Arg | Ala | Ser | |
| TCG | CGC | TGC | CAG | AGC | ACC | AAA | TCT | GCC | CAG | TCC | ACG | CGT | 1273 |
| Ser | Arg | Cys | Gln | Ser | Thr | Lys | Ser | Ala | Gln | Ser | Thr | Arg | |
| TCC | AGC | CGC | TCC | ACA | CGC | TCC | AAT | AAG | TCA | CGC | CGT | GTG | 1312 |
| Ser | Ser | Arg | Ser | Thr | Arg | Ser | Asn | Lys | Ser | Arg | Arg | Val | |
| CGG | GAA | CGG | GAG | CTG | CGG | GAG | CTC | AAC | CTG | CGC | TAC | CAG | 1351 |
| Arg | Glu | Arg | Glu | Leu | Arg | Glu | Leu | Asn | Leu | Arg | Tyr | Gln | |
| CAG | CAA | TAC | AAT | GGC | TGAGCCGAATGGCTGTGCACACATGCAGCA | | | | | | | | 1396 |
| Gln | Gln | Tyr | Asn | Gly | (SEQ ID NO:2) | | | | | | | | |

| | |
|---|---|
| CGACCCAGCCTGGCCACACACTGTGGTGCCATCTGGGTCCGATGCCCTCTC | 1447 |
| TGGAGATAGGCCTATGTGGCCCACAGTAGGTGAAGAATGTCTGGCTCCAGC | 1498 |
| CCTTTCTCTGTCGGTTCACCAGCCCCTGTCCTCACCATGGGCCTGGGCCAG | 1549 |
| GTGTGACAGAGTAGAGGTAGCACAGGGGGCTGTCCTCACCATGGGCCTGGG | 1600 |
| CCAGGTGTGACAGAGTAGAGGTAGCACAGGGGGCTGTGACTCCCCCTGAAC | 1651 |
| TGGGAGCCTGGCCTGGCAGTGATACCCCTCTTGGTGGGCAGCTGCTCTGGT | 1702 |
| GGAGTTGGGAAGGGATAGGACCTGGCCTTCACTGTCTCCCTTGCCCTTTGA | 1753 |
| CTTTTCCCCAATCAAAGGGAACTGCAGTGCTGGGTGGAGTGTCCTGTCGCC | 1804 |
| TCAGGACCCTTTGGGACAGTTACTTCTGGGACCCCCTTTCCTCCACAGAGC | 1855 |
| CCTTCTCCCTCCTTTCACACATTCCCATGCATCCTGATCCTTAAGATTATG | 1906 |
| CTCCAGTGGGAGACCCTGGTAGGCACAAAGCTTGTGCCTTGACTGGACCCG | 1957 |

TABLE I-continued

| | |
|---|---|
| TAGCCCCTGGCTAGGTCGAAACAGCCCTCCACCTCCCAGCCAAGATCTGTC | 2008 |
| TTCCTTCATGGTGCCTCCAGGGAGCCTTCCTGGTCCCAGGACCTCTGGTGG | 2059 |
| AGGGCCATGGCGTGGACCTTCACCCTTCTGGACTGTGTGGCCATGCTGGTC | 2110 |
| ATCGGCTTGCCCAGGCTCCAGCCTCTCCAGATTCTGAGGGGTCTCAGCCCA | 2161 |
| CCGCCCTTGGTGCCTTCTTTGTAGAGCCCACCGCTACCTCCCTCTCCCCGT | 2212 |
| TGGATGTCCATTCCATTCCCCAGGTGCCTCCTTCCCAACTGGGGGTGGTTA | 2263 |
| AAGGGACGCCCACTGCTGCTACCTGGGGAATGGGGCACCTGGGGCCCAAGG | 2314 |
| CAGAGGGAAGGGGGTCCTCCCGATTAGGGTCGAGTGTCAGCCTGGGTTCTA | 2365 |
| TCCTTTGGTGCAGCCCCATTGCCTTTTCCCTTCAGGCTCTGTTGCTCCCTC | 2416 |
| CTCTGCAGCTGCACGAAGGCGCCATCTGGTGTCTGCATGGGTGTTGGCAGC | 2467 |
| CTGGGAGTGATCACTGCACGCCCATCCTCCACACCTGCCCATCGTGCACAC | 2518 |
| CCACCCATGGTGCACACCTGTAGTCCTCCATGAGGACATGGGAAGGTAGGA | 2569 |
| GTTGCCGCCCTGGGGGAGGGTCCCGGGCTGCTCACCTCTCCCCTTCTGCTG | 2620 |
| AGCTTCTGCGCACCCCTCCCTGGAACTTAGCCATACTGTGTGACCTGCCTC | 2671 |
| TGAAACCAGGGTGCCAGGGGCACTGCCTTCTCACAGCTGGCCTTGCCCCGT | 2722 |
| CCACCCTGTGCTGCTTCCCTTCACAGCATTAACCTTCCAGTCTGGGTCCCA | 2773 |
| CTGAGCCTCAAGCTGGAAGGAGCCCCTGCGGGAGGTGGGTGGGGTTGGGTG | 2824 |
| GCTGCTTTCCCAGAGGCCTGACGCCAGAACCATCCCCATTTCTTTTGTGGT | 2875 |
| ATCTCCCCTACCACAAACCAGGCTGGAACCCAAGCCCCTTCCTCCACAGC | 2926 |
| TGCCTTCAGTGGGTAGAATGGGGCCAGGGCCCAGCTTTGGCCTTAGCTTGA | 2977 |
| CGGCAGGGCCCCTGCCATTGCACGAGGGTTTGGTTCCCACTCAGCTTCTCC | 3028 |
| GGTCGGCAGCCTGGGCCAGGCCCTTTTCCTGCATGTGCCACCTCCAGTGGG | 3079 |
| AAACAAAACTAAAGAGACCACTCTGTGCCAAGTCGACTATGCCTTAGACAC | 3130 |
| ATCCTCCTACCGTCCCCAATGCCCTGGGCAGGAGGCAGTGGAGAACCAAG | 3181 |
| CCCCATGGCCTCAGAATTTCCCCCCAGTTCCCCAAGTGTCTCTGGGGACCT | 3232 |
| GAAGCCCTGGGGCTTACGTTCTCTCTTGCCCAGGGTGGCCTGGTCCTGAGG | 3283 |
| GCAGGACAGGGGGTTTGCAGATGTGGGCCTTTGATAGACCCACTTGGGCCT | 3334 |
| TCATGCCATGGCCTGTGGATGGAGAATGTGCAGTTATTTATTATGCGTATT | 3385 |

TABLE I-continued

| | |
|---|---|
| CAGTTTGTAAACGTATCCTCTGTATTCAGTAAACAGGCTGCCTCTCCAGGG | 3436 |
| AGGGCTGCCATTCATTCCAACAAAAAAAAAAAAAA (SEQ ID NO:1) | 3471 |

The nucleotide sequence 95–3471 was described in the European Molecular Biology Laboratory (EMBL) release referred to in Larsen et al., Hum. Mol. Gen. 2(10):1589–1595 (1993). The nucleotide sequence 687–1138 and the deduced amino acid sequence were reported in Hanks, Proc. Natl. Acad. Sci. USA 84:388–392 (1987). However, the Larsen publication fails to disclose nucleotides 1–94, which constitute a 30 nucleotide exon 1 and a 64 nucleotide addition to what was reported in Larsen as the first coding exon of the gene. See page 1590 of Larsen. Even though the present inventor had succeeded in cloning a relatively large portion of the PSKH-1 gene, the elucidation of the 94 nucleotide sequence containing the first exon presented unusual difficulties, due in large part to the relative size of the first intron (about 10 kb in length) compared to the first exon, and the presence of a CpG island in the region of the 5' regulatory sequence/first exon.

PSKH-1 DNA may be prepared in accordance with standard procedures such as miniprep methods. A construct for the expression of PSKH-1 protein can be prepared using standard recombinant DNA techniques. See, e.g., J. Sambrook et. al., "Molecular Cloning; A Laboratory Manual" (1989); "DNA Cloning", Vols. I and II (D. N. Glover ed. 1985). PSKH-1 can be expressed in a variety of hosts, including both prokaryotes and eukaryotes such as bacteria, yeasts, and mammalian cells. Appropriate 5' and 3' regulatory sequences and the vector and transformation procedure are chosen on the basis of the given hosts. Preferred vectors include Bluescript (Stratagene), pcDNA3, pMAL, pGST, and PSFV 1 (Semliki Forest Virus). A preferred host cell is E. coli. More preferred are mammalian immortalized cell lines such as baby hamster kidney (BHK) cells, HeLa. cells and Chinese hamster ovary (CHO) cells. These cell lines are available from the ATCC.

Following expression, the PSKH-1 protein can be purified to the extent desired in accordance with standard purification procedures known in the art. Representative purification schemes include ultrafiltration, gel electrophoresis, gel filtration, ammonium sulfate precipitation, and chromatographic techniques such as ion exchange chromatography, size exclusion chromatography, HPLC, reverse phase HPLC, hydroxyapatite, affinity chromatography, e.g., immunosorbent chromatography, and the like.. PSKH-1 protein, or antigenic fragments thereof, are used to prepare anti-PSKH-1 antibodies for use in assays to determine the cellular localization of PSKH-1, as well as to measure the specificity of the ribozymes of the present invention.

Yet another aspect of the present invention is directed to ribozymes that cleave PSKH-1 pre-mRNA or mRNA. The ribozymes are designed based upon the PSKH-1 DNA sequence. Until 1981, it had been axiomatic that all enzymes were composed of proteins. Investigators discovered that ribosomal RNA precursor of tetrahymena, a protozoan, expels an intron (IVS) unnecessary for the transfer of gene information by self-splicing without the aid of any protein. See Cech et al., Nature 308:820–825 (1984). Ribozymes are typically RNA molecules having an enzymatic activity which is able to repeatedly cleave other separate RNA target molecules in a nucleotide base sequence specific manner, blocking their expression and with affecting normal functions of other genes. Ribozymes can be targeted to virtually any RNA transcript, and achieve efficient cleavage in vitro. See Kim et al., Proc. Natl. Acad. Sci. USA 84:8788–8792 (1987), Haseloff et al., Nature 334:585–591 (1988), Cech, JAMA 260(20):3030–3034 (1988), and Jefferies et al., Nucl. Acad. Res. 1989, 17, 1371. Ribozymes act by first binding to a target RNA. Such binding occurs through the target RNA binding portion of the ribozyme, which is held in close proximity to an enzymatic portion of the RNA which acts to cleave the target RNA. Thus, the ribozyme first recognizes and then binds a target RNA by complementary base-pairing. Once bound to the correct site, it then acts enzymatically to cut the target RNA. Strategic cleavage of the target RNA will destroy its ability to direct synthesis of an encoded protein. After the ribozyme has bound and cleaved its target RNA, it is released from that target RNA such that it searches other targets and such can repeatedly bind and cleave different nucleotides of the same target RNAs.

In preferred embodiments, the ribozymes of the present invention may be formed in various motifs, such as the motif of a hammerhead, hairpin, or hepatitis delta virus in association with an RNA guide sequence. Hammerhead ribozymes, which are particularly preferred, are members of classes related to the replication cycle of a group of self-replicating RNAs called viroid-like pathogens (VLPs). The hammerhead ribozymes are made up of three base paired stems and a core of highly conserved, non-complementary nucleotides essential for catalysis. See Cech et al., Nature 372:39–40 (1994). This catalytic motif is commonly referred to as the "hammerhead", and typically consists of about 23 nucleotides. The three-dimensional structure of hammerhead ribozymes and their mode of action or requirements for cleavage have been elucidated. See, e.g., Uhlenbeck, Nature 328:596–600 (1987), Forster et al., Cell 50:9–16 (1987), Pley et al., Nature 372:68–74 (1994), and Tuschl et al., Science 266:785–789 (1994). See also U.S. Pat. Nos. 5,436,330, 5,246,921, 5,496,698, and 5,144,019. These ribozymes will catalyze cleavage of target RNA in the presence of $Mg^{2+}$. Pyle, Science 261:709–714 (1993). Commercial application of hammerhead ribozymes has also been described in WO 90/05852, published Jun. 29, 1989. Hammerhead ribozyme activity is targeted to a specific mRNA or pre-mRNA. (i.e., which contains introns) by choosing the sequences flanking the catalytic motif. Given that hammerhead ribozymes have a propensity for cleaving target mRNAs after, e.g., the base sequence GUC, hammerhead ribozymes may be customized by including complementary sequences to the 5' and 3' base sequences that flank the cleavage site. Hammerhead ribozymes may have specificity for several other RNA triplets, including GUA, GUG, GUU and AUU.

FIG. 1 schematically illustrates the secondary structure of the complex formed between a preferred hammerhead ribozyme of the present invention (denoted as SEQ ID NO:8) and ribonucleotides 136–149 of the PSKH-1 RNA (denoted as SEQ ID NO:4). The PSKH-1 ribozyme contains a single strand chain of 35 bases or ribonucleotides, as follows:

(SEQ ID NO:3)

5' ACAGCUGCUgaUgAGGCCGUUAGGCCgAAaCAU$_{PS}$C$_{PS}$C 3'.

All of the ribonucleotides except for nos. 10, 11, 13, 27 and 30 (counting from the 5' end) are modified in that they are substituted with an allyl group in the 2' position. The three 3' ribonucleotides are linked together via phosphorothioate links instead of phosphodiester links. The hammerhead portion of the ribozyme consists of bases 8–30. The ribozyme also comprises a succession of bases at each end which is complementary to six bases in the sequence of the PSKH-1 mRNA (i.e., bp's 136–141 and 143–148), such that the ribozyme contains twelve bases that are complementary to the PSKH-1 mRNA. Located between these two six base regions in the PSKH-1 mRNA is a GUC triplet sequence which is the target for the ribozyme (i.e., the bond between cytosine nucleotides 142 and 143). The ribozyme cleaves the PSKH-1 pre-mRNA and mRNA at this triplet. Aside from the most 5' and 3' bases of the ribozyme which must be complementary to the RNA target, the hammerhead portion of the PSKH-1 ribozyme depicted in FIG. 1 may be represented generically by the following sequence:

5' CUgaNgA(N)$_x$NNNN(N')$_x$gAAa 3' (SEQ ID NO:5), wherein N represents A, C, G, or U; N' represents a ribonucleotide, e.g., A, C, G or U, complementary to base (N)$_x$ to allow for the formation of Watson-Crick hydrogen bonding; and x=2, 3 or 4.

Figure 2:
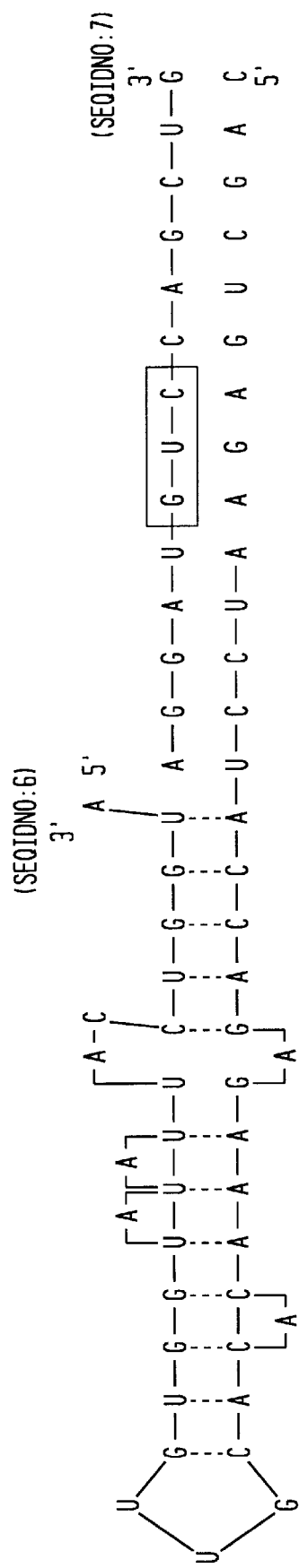
FIG. 2 is a schematic diagram of the secondary structure of a complex between a hairpin ribozyme of the present invention (denoted as SEQ ID NO:6)and a specific sequence of PSKH-1 RNA (denoted SEQ ID NO:7) (bases in bold), wherein the (- - -) represent Watson-Crick hydrogen bonding.

Ribozymes of the hairpin motif are characterized by a hairpin-like configuration when the target RNA-ribozyme complex is modeled in two dimension for minimum energy folding. The "hairpin" portion typically is not an absolute hairpin in the sense that not all bases of the hairpin portion are base-paired. The catalytic complex is a complex of the minimum, or substantially the minimum, sequence of the catalyst necessary for activity and the minimum, or substantially the minimum, target sequence of the substrate RNA. To design a hairpin ribozyme, the bases flanking the cleavage sequence must be identified and the ribozyme engineered so that it does not pair in two-dimensional space with the cleavage sequence, but instead pairs with adequate numbers of flanking bases upstream and downstream of the cleavage sequence. Teachings of the design of hairpin ribozymes are disclosed, for example, in Hampel et al., 28 Biochemistry 4929, 1989; Hampel et al., 18 Nucleic Acid Research 299, 1990; and U.S. Pat. No. 5,527,895. A preferred hairpin ribozyme is depicted schematically in FIG. 2. A preferred cleavage site is 5' NGUC 3', specifically the bond between ribonucleotides N 40 and G, as illustrated in FIG. 2 with the PSKH-1 RNA sequence 135–148 (denoted in FIG. 2 as SEQ ID NO:7)(the cleavage site being the bond between the uracil and guanine ribonucleotides at positions 139 and 140, respectively). In general, aside from the most 5' ribonucleotides which must be complementary to the target site and its 5' and 3' flanking sequences, the ribonucleotides in the stems or helices (i.e., bases 15–50 counting from the 5' end of the ribozyme) may be exchanged provided that complementarity (to allow for the hydrogen bonding) is preserved.

The types of ribozymes discussed above are not limiting in the invention. All that is necessary is that the ribozyme has a specific substrate binding site which is complementary to one or more of the target PSKH-1 mRNA or pre-mRNA regions, and that it has nucleotide sequences within or surrounding the PSKH-1 mNA binding site which impart an RNA cleaving activity to the ribozyme. The ribozymes of the present invention may be prepared by recombinant techniques or chemical synthesis. The procedure of choice will depend in part on whether the ribozyme contains modified ribonucleotides as these must be linked to the ribozyme chain via chemical means. See, e.g., U.S. Pat. Nos. 5,272,262, 5,144,019 and 5,246,921. Chemical synthesis is preferred.

A further aspect of the present invention is directed to the use of ribozymes that cleave PSKH-1 mRNA or pre-mRNA in the treatment of patients suffering from diseases or medical conditions characterized by uncontrolled cell proliferation or growth. Representative diseases and medical conditions include cancers or malignancies, such as carcinomas of the brain, heart, colon, rectum, bladder, kidney, liver, lung, ovary, pancreas and stomach, hematopoietic tumors of lymphoid and myeloid lineage, as well as non-malignant disease conditions such as autoimmune diseases (i.e., which involve uncontrolled B-or T-cell proliferation), allograft rejection and atherosclerosis development.

The ribozymes of the present invention can be delivered to the target cells, i.e., those that are undergoing abnormal proliferation or growth, in accordance with drug delivery modes known in the art. For example, disease tissue-specific delivery may be accomplished by utilizing lipid delivery systems such as targeted liposomes (see, e.g., U.S. Pat. Nos. 5,144,019 and 5,459,127, and Felgner et al., Proc. Natl. Acad. Sci. USA 84:7413–7417 (1987)) or simply by injection of an aqueous solution of the ribozyme directly into a tumor or disease situs. Other representative delivery modes include slow-release devices such as micropumps, biodegradable vehicles, and alginates having defined pore sizes. In a preferred embodiment wherein the composition contains the hammerhead ribozyme schematically illustrated in FIG. 1 which is sufficiently hydrophobic so as to be internalized by the target cells on its own, i.e., without a liposome-type vehicle, the composition is provided simply in the form of an aqueous solution in a slow-release device. One main advantage of the compositions and methods of the present invention is that they do not require the aid of target-specific ligands in which to direct the ribozymes to the target (diseased) cells and not to non-diseased cells. While not intending to be bound by any particular theory of operation, the present inventors believe that PSKH-1 is expressed and present in actively dividing cells, and that the enzyme is not present in normal, differentiated (i.e., $G_0$ state) cells.

In addition, because of their specific and catalytic mode of action, the ribozymes of the present invention are ideal agents for therapeutic intervention in diseases characterized by uncontrolled cell growth or proliferation. In addition, the enzymatic nature of the ribozymes is advantageous over other technologies such as antisense technology (i.e., where a nucleic acid molecule simply binds to a nucleic acid target to block its translation), because the effective concentration of ribozyme necessary to effect a therapeutic treatment is lower than that of antisense oligonucleotide. This advantage reflects the ability of the ribozyme to act enzymatically. Thus, a single ribozyme molecule is able to cleave many molecules of target PSKH-1 MRNA. The therapeutically effective amount of the ribozyme can be determined in accordance with standard techniques. See U.S. Pat. No. 5,246,921. In general, the ribozymes of the present invention are administered in doses of about 1 to about 10 mg/kg of body weight per day.

Further, the ribozyme is a highly specific inhibitor, with the specificity of inhibition depending not only on the base pairing mechanism of binding, but also on the mechanism by which the molecule inhibits the expression of the PSKH-1 mRNA. That is, the inhibition is caused by the cleavage of the PSKH-1 mRNA and so specificity is defined as the ratio of the rate of cleavage of the PSKH-1 mRNA over the rate of cleavage of non-targeted RNA. Thus, it is thought that the specificity of action of the ribozymes of the present invention is greater than that of an antisense oligonucleotide binding the same PSKH-1 mRNA site.

The invention will be further described by reference to the following detailed examples. These examples are provided for purposes of illustration only, and are not intended to be limiting unless otherwise specified. Unless otherwise indicated, all parts are by weight.

EXAMPLE 1

Determination Of The sequence of Full Length PSKR-1 cDNA

The determination of the sequence of the 5' end of PSKH-1 cDNA was conducted using 5' RACE™ technology, as follows. The first primer, 5' GTGTGCAT-ACTGACTTGCTG 3' (SEQ ID NO:8), was placed 160 bp downstream of the ATG start codon of the PSKH-1 cDNA. The second primer, 5' TCCACCTCTGTGATGAAGTG 3' (SEQ ID NO:9), was placed 108 bp downstream of the ATG start codon. The first primer was used for the first strand cDNA synthesis.

The polyA-mRNA template used for the synthesis was isolated from 2×10⁶ HeLa cells by the direct oligo dT-Dynabead method, in accordance with the manufacturer's instructions. 0.25 ml of Dynabeads® Oligo (dT)$_{25}$ (kit provided by Dynal, Oslo, Norway) were resuspended and then transferred to an RNase-free Eppendorf tube placed in Dynal MPC (Dynal MPC-E/Dynal MPC-M). The supernatant was removed when the suspension became clear. The vial was removed from the Dynal MPC and the Dynabeads® Oligo (dT)$_{25}$ were prewashed by resuspending them in lysis/binding buffer (0.2 ml), and then placed in the Dynal MPC. The HeLa cell suspension was washed in phosphate-buffered saline (1×PBS), and then centrifuged to prepare a cell pellet. 1.0 ml of lysis/binding buffer was added to the pellet (1–4×10⁶). The viscosity of the thus-obtained crude cell lysate was reduced by a DNA-shear step wherein the lysate was pressed three times through a 21 gauge needle by 1–2 ml syringe using force.

The lysis/binding buffer was removed from the Dynabeads® Oligo (dT)$_{25}$ vial. The vial was then transferred from the Dynal MPC to another rack in order to add the lysate. The Dynabeads® Oligo (dT)$_{25}$ were mixed with the lysate and then annealed by rotating on a roller for 3–5 minutes at room temperature. The vial was then placed in the Dynal MPC for two minutes, then the supernatant was removed. The Dynabeads® Oligo (dT)$_{25}$ were washed twice with washing buffer containing LiDS (0.5–1 ml) at room temperature using the Dynal MPC, and then once with washing buffer alone (0.5 ml). To elute the mRNA from the Dynabeads® Oligo (dT)$_{25}$, 10–20 μl of the elution solution (in the kit provided by the manufacturer) were added, and the resulting mixture was maintained for two minutes at 65° C. The mixture tube was placed in Dynal MPC, and the supernatant containing the mRNA was transferred to a new RNase-free tube.

2 μg of the thus-obtained mRNA were used as a template in the 5' RACE reaction using the 5'-Ampli FINDER™ RACE Kit (Clontech Laboratories, Inc. Palo Alto, Calif.), in accordance with the manufacturer's instructions. To synthesize PSKH-1 CDNA, the following reverse transcription master mixture was prepared in a 0.5 ml sterile microcentrifuge tube:

| | |
|---|---|
| 9.2 μl | DEPC-treated H$_2$O |
| 9 μl | 4X Reverse transcriplase buffer* |
| | *warm by hand until all buffer components dissolve |
| 1.6 μl | RNAse inhibitor (40 units/μl) |
| 3.7 μl | Ultrapure dNTP mix (10 mM) |
| 0.5 μl | AMV reverse transcriptase (25 units/μl) |
| 24.0 μl | Total Volume | cDNA synthesis was primed by mixing 2 μg poly A⁺ RNA, 1 μl cDNA synthesis primer (10 μm), and 2–3 μL DEPC-treated H$_2$O (depending on the volume of RNA) to a total volume of 10 μl, in a 0.5 ml microcentrifuge tube, and preincubating the thus-prepared mixture for five minutes at 65° C. The reverse transcription reaction was initiated by adding 20 μl of the reverse transcription master mix, to prepare a 30 μl CDNA reaction mixture. The resultant mixture was incubated for 30 minutes at 52° C., and 1 μl of 0.5M EDTA was added, followed by vortexing.

To hydrolyze the RNA, 2 μl of 6M NaOH were added to the 30 μl of the cDNA reaction mixture. The resultant mixture was vortexed, spun down, and then incubated for 30 minutes in a heat block set at 65° C., followed by a brief spin down. 2 μl of 6M acetic acid were added, followed by vortexing, and then 80 μl of the 6M NaI solution were added followed by vigorous vortexing. The contents were then transferred to a 1.5-ml centrifuge tube.

To purify the cDNA, 8 μl GENO-BIND™ suspension (Clontech, Palo Alto, Calif.) were added to the cDNA reaction mixture. The contents were vortexed and kept on ice for ten minutes with occasional vortexing. The tube was then centrifuged at 4° C. at full speed (i.e., 15,000 rpm or 12,000×g) for ten seconds. The supernatant was carefully removed, and 500 μl of 80% EtOH were added under vigorous vortexing to completely resuspend the GENO-BIND™. The centrifugation and resuspension steps were repeated, followed by centrifugation at 4° C. for 30 seconds at full speed. The supernatant was removed and the pellet was allowed to air dry for five minutes. 15 μl of DEPC-treated H$_2$O were added. The pellet was completely resuspended and incubated in a heatblock set at 65° C. for five minutes. The tube was spun at full speed at room temperature for two minutes. 45 μl of the supernatant containing the cDNA were removed and placed in a fresh 1.5-ml microcentrifuge tube.

To precipitate the cDNA, 2.5 μl glycogen solution (carrier), 5 μl of 2M sodium acetate, and 100 μl of 95% EtOH were added to the cDNA, and the resultant mixture was incubated at −20° C. for 30 minutes. The tube was centrifuged at 13,000 rpm for ten minutes at 4° C. The supernatant was removed, and the pellet was rinsed with 40 μl of 80% EtOH so as not to disturb the pellet, followed by centrifuging at 15,000 rpm for an additional two minutes. The supernatant was removed and the pellet was air-dried for five minutes, and resuspended in 6 μl of DEPC-treated H$_2$O.

The following mixture was prepared for each anchor ligation performed: 2.5 μl cDNA; 2 μl Ampli FINDER™ Anchor Sequence 3'NH$_3$ GGAGACTTCCAAGGTCTTAGCTATCACTTAAGCAC-P 5' (SEQ ID NO:10)(4 pmol); 5 μl 2×single-stranded ligation buffer; and 0.5 µl T4 RNA ligase (20 units/µl, to a total volume of 10 µl. The solution was mixed well, and incubated at 37° C. for 6–8 hours. The thus-ligated CDNA was diluted 10×, and 1 µl of the diluted CDNA was used for PCR.

The PCR reactions were carried in a DNA Thermal Cycler (PERKIN-EIMER CETUS) using PCR reaction tubes (Treff AG, Degersheim, Switzerland). The following components were placed into each PCR reaction tube:

(SEQ ID NO:12)
5'—|CTGGTTCGGCCCA| CCTCTGAAGGTTCCAGAATCGATAG-3'

In addition to the anchor primer (1 µl), the above mixture contains 1 µl of the primer 5' TCCACCTCTGTGAT-GAAGTG 3' (SEQ ID NO:11). That is, the primer 2 is added to the PCR mix. The other primer present is the anchor primer sequence (SEQ ID NO:12)
5'—|CTGGTTCGGCCCA| CCTCTGAAGGTTCCAGAATCGATAG-3' provided with the kit that is complementary to the anchor sequence ligated onto the cDNA. The reaction mixture was overlaid with mineral oil and caps were placed on the tubes. The tubes were heated for one minute at 82° C. The tubes were opened and 0.5 µl (i.e., 2.5 units) of TAQ DNA polymerase were injected under the mineral oil layer overlaying the solutions. The tubes were quickly capped and thermocycling was commenced immediately using the following parameters:

94° C. Denature 45 sec;

60° C. Anneal 45 sec; and

72° C. Extend 2 min.

A total of 35 cycles were run, with a final extension time of seven minutes for all amplifications with the anchor primer.

The resultant PCR product was subjected to agarose gel electrophoresis and was determined to have about 260 bp. The product was purified by a 1-step PCR purification package kit (Advanced Genetic Technologies Corp., Gaithersburg, Md.), in accordance with the manufacturer's instructions.

The PCR product was ligated into the pXT vector and sequenced by the Sanger dideoxy method using fluorescent DATP (Boehrihger) and the ALF (Pharmacia) semiautomated sequencer. Six identical clones were found, extending the sequence with 94 bp upstream of the ATG. Referring again to SEQ ID NO:1, above, the 64 bp immediately upstream of the ATG were identical to a genomic sequence obtained earlier from a plasmid subclone of a cosmid and adds onto the 5' end of exon 2. The 30 bp sequence most 5' in the cDNA was identical to a sequence in a 900 bp genomic PstI fragment located about 10 kb upstream of exon 2 and constitutes a new exon 1 of the PSKH-1 gene. The determination of this exon 1 was complicated by the fact that there is an 8 base sequence at the 3' end of exon I which is directly repeated at the 3' end of intron 1. Intron 1 ends with the expected AG dinucleotide.

EXAMPLE 2

Expression and Purification of PSKH-1

PSKH-1 CDNA was cloned into PSFV1 (Semliki Forest Virus) plasmid vector (Gibco BRL) which served as a template for the in vitro synthesis of recombinant PSKH-1 RNA. Cloning and synthesis of recombinant RNA were then carried out. Recombinant PSKH-1 RNA was packaged in vivo into infectious virus particles aided by RNA from Helper 1 packaging-defective virus in a cotransfection mode using electroporation as described in Liljestrom & Garoff, BIO/TECHNOLOGY 9:1356–1361 (1991). The packaged virus was then used to infect BHK-21 cells (ATCC CRL 8544) that were harvested after 36 hours. All infections were checked in parallel immunoflurescence experiments to ensure that all cells were infected.

Following incubation for 2 hours at room temperature, the cells were removed from the medium and washed with 10 ml PBS. 1 ml of lysis buffer was added and the reaction mixture was allowed to stand on ice for 10–20 minutes. The lysis buffer consisted of 1% (v/v) Nonidet P-40, 50 mM Tris-HCL (pH 7.6), 150 mM NaCl, and a Protease Inhibitor Cocktail containing 50 mM PMSF, 5.5 U/ml aprotinin, 0.5 mg/ml leupeptin, 0.5 mg/ml antipain, 0.5 mg/ml chymostatin, 0.5 mg/ml phosforamidon, and 250 mM EDTA. The cells were removed from the medium and washed with 10 ml PBS. The cells were resuspended and transferred into Eppendorf tubes, and centrifuged at 13,000 rpm for 10 minutes. The supernatant was collected and aliquots were distributed in several Eppendorf tubes and stored at −80° C. 10 ml of PSKH-lysate contained approximately 530 mg total protein.

To purify PSKH-1, the protein-lysate was subjected to the sequential steps of ammonium sulfate precipitation, gel filtration chromatography and hydroxyapatite chromatography. The saturated ammonium sulfate solution contained 167.33 gm lysate dissolved in 300 ml of 10 mM Tris, pH 7.5. The proteins in the cell lysate were precipitated by adding ammonium sulfate at 35% and 60% saturation, in an ice bath with constant stirring. The precipitates were resuspended with 50 mM ammonium bicarbonate (pH 7.8) and were tested by SDS/PAGE and Western-blotting. Both precipitates gave a positive signal in the Western Blot indicating the presence of PSKH-1 protein. Approximately 158 mg total protein was obtained with the 35% ammonium sulfate saturation, whereas 4 mg total protein were obtained using 35% ammonium sulfate saturation followed by 60% ammonium sulfate saturation.

The precipitates from the ammonium sulfate fractionation purification step were then subjected to gel filtration using 16 mm×60 cm Superdex 75 column (Pharmacia, Sweden). Between 1 and 5 ml of each precipitate was applied to the gel filtration column separately at a flow rate of 1–2 ml/min. The precipitates were applied to the column mixed with buffer which was either 50 mM ammonium bicarbonate (pH 7.8) or 10 mM sodium phosphate (pH 6.8). Each fraction collected was tested by SDS/PAGE and Western Blot. Fractions which gave positive signals for PSKH-1 were pooled. Approximately 3 mg of protein were obtained from the 35% ammonium sulfate saturation and approximately 4 mg PSKH-1 protein were obtained from the fraction derived from the 60% ammonium sulfate saturation precipitate. The PSKH-1 protein recovered from this step represented a 100-fold increase in purification.

The pooled fractions from the gel-filtration step were then subject to hydroxyapatite chromatography using a 10 mm×64 mm Bio-scale CHT 5-i Hydroxyapatite column (Biorad, Richmond, Calif.) at a bed volume of 5 ml and a maximum operating column pressure of 750 psi and a maximum protein load of 50 mg. The pooled fractions were applied to the column with 10 mM sodium phosphate (pH 6.8), and were eluted with a gradient of 0–80% of 500 mM sodium phosphate (pH 6.8) for 20 minutes at a flow rate of 2 ml/min., and monitored at an optical density of 280 nm. Total PSKH-1 protein was recovered relatively early in the chromatogram (i.e., elution time less than 5 minutes).

EXAMPLE 3

Cellular Localization of PSKH-1

Having the full-length nucleotide and amino acid sequences of PSKH-1 at hand, only now could the localization of the enzyme in the cell could be determined. Based on the amino acid sequence of PSKH-1, the following amino acid sequence was identified as an antigenic peptide sequence:

N-K-S-R-R-V-R-E-R-E-L-R-E-L-N-L-R-Y-Q-Q (SEQ ID NO:12), which corresponds to amino acids 401–420 of PSKH-1 protein in SEQ ID NO:2, above. The antigenic sequence was chosen on the basis of its high hydrophilicity score using the Kyte-Doolittle hydropathy plot (Kyte et al., J. Mol. Biol. 157:105 (1982)) and the Jameson-Wolfe algorithm, as described in Comput. Appl. Biosci. 4:181 (1988).

The peptides were synthesized on an ABI 430A peptide synthesizer (Applied Biosystems, Inc., CA), linked to the carrier protein keyhole limpet hemocyanine (KLH), and the resultant peptide-carrier complex was injected into rabbits to produce antibodies specific to the antigenic peptide sequence.

To conduct the cell localization experiment, COS-1 monkey kidney cells (ATCC CRL 1650) were grown on cover slips for ten hours, fixed in methanol for five minutes at −20° C., and then washed once in PBS. The cells were then blocked in 20% fetal calf serum for ten minutes at room temperature. The cells were incubated with the primary antibody, i.e., 30 $\mu$l of anti-PSKH-1 antibody, diluted 1/100 in PBS, for 30 minutes at room temperature. As a positive control, the cells were incubated with 30 $\mu$l of the primary antibody CTR 453 which is directed to a known centrosome structure described in Bornens et al., Cell Motility & Cytoskeleton 8:239–249 (1987). The thus-incubated cells were washed five. times in PBS, followed by incubation with secondary antibodies specific for each of the two primary antibodies. The secondary antibody specific to anti-PSKH-1 was FITC-labeled SAR (Dakopatts, Denmark, Code F205, lot 030), diluted 1/100 in PBS, which produced a green fluorescence. The secondary antibody specific to CTR 453 was TRITC-labeled rabbit anti-mouse IgG, diluted ¼ in PBS, which produces a red fluorescence. Following the incubation, which was conducted for 30 minutes, the cells were washed five times in PBS, air dried for one minute, and mounted with mowiol before immunofluorescence microscopy. Slides were taken using Fujichrome 400 ASA.

Figure 3A:
FIG. 3A is a microphotograph that illustrates using red fluorescence the centrosomal location in Cos-1 cells of a monoclonal antibody known to react with centrosomes.
Figure 3B:
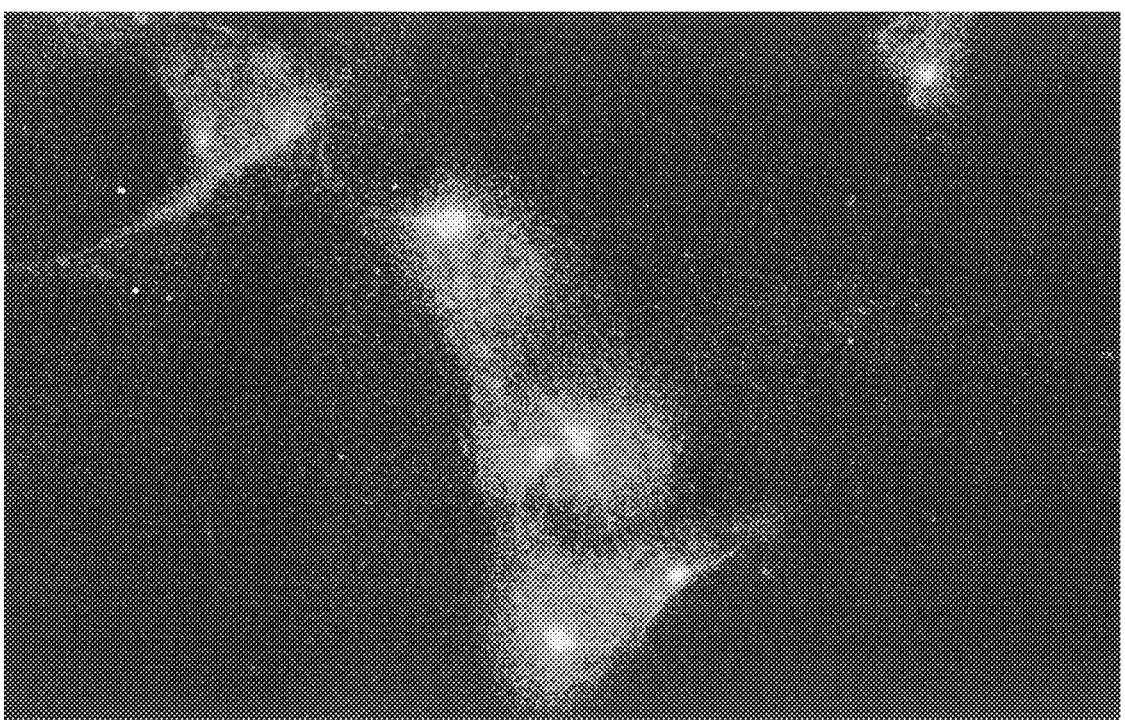
FIG. 3B is a microphotograph that illustrates using green fluorescence the centrosomal localization of anti-PSKH-1 in the same Cos-1 cells.

The localization of PSKH-1 in the centrosomes of the COS-1 cells is illustrated in FIGS. 3A and 3B. These microphotographs demonstrate that the FITC-labeled secondary antibody specific to anti-PSKH-1 has the same location in the cells as TRITC-Rhodamine-labeled CTR 453 which is known to be specific to centrosomes.

EXAMPLE 4

Inactivation of PSKH-1 MRNA Halts Cell Division

The building blocks used to synthesize the PSKH-1 hammerhead ribozyme depicted in FIG. 1 were 2'-0-allylribonucleotides (Boehringer-Mannheim) and 2'-0-tertbutyldimethylsilyl protected ribonucleotides. The hammerhead ribozyme was synthesized on solid phase using phosphoramidite chemistry and neat triethylamine trihydrofluoride deprotection of the partially deprotected oligomer. The product was purified by HPLC.

50 $\mu$g of the PSKH-1 hammerhead ribozyme and 1–2×10$^6$ HL-60 cells (ATCC CCL 240) in a volume of 1 ml were incubated for from 30 minutes to 1 hour at 37° C. and then stained with propidium iodide to determine DNA content. As a first control, an incubation was conducted with HL-60 cells and an enzymatically inactive analogue, 5' A C A G C U G C U a a U g A G G C C G U U A G G C - CgAAaCAU$_{PS}$C$_{PS}$C 3' (SEQ ID NO:14)(wherein the "g" at position 27 of the PSKH-1 ribozyme above was changed to an "a"), and also with a ribozyme capable of cleaving amelogenin mRNA (Lyngstadaas et al., EMBO J. 14(21) :5224–5229 (1995)), and an oligonucleotide with a random RNA sequence.

Figure 4A:
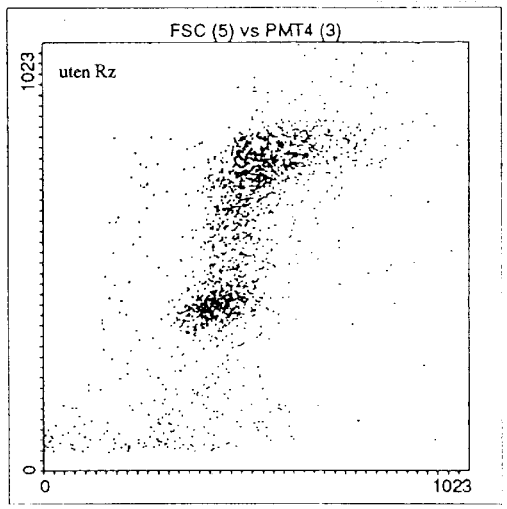
FIGS. 4A, 4B, 4C, and 4D are graphs prepared from results obtained from flow cytometric measurements on the number of HL-60 cells stained with propidium iodide and treated with random oligonucleotide (FIG. 4A), ribozyme specific to amelogenin (4B), catalytically inactive ribozyme (4C), and ribozyme specific to PSKH-1 (4D), versus the fluorescence intensity.
Figure 4B:
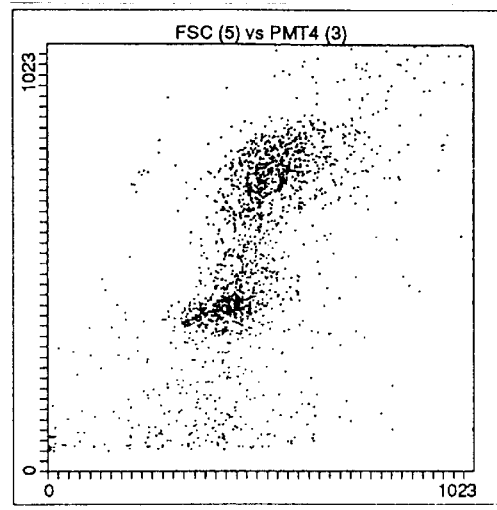
Figure 4C:
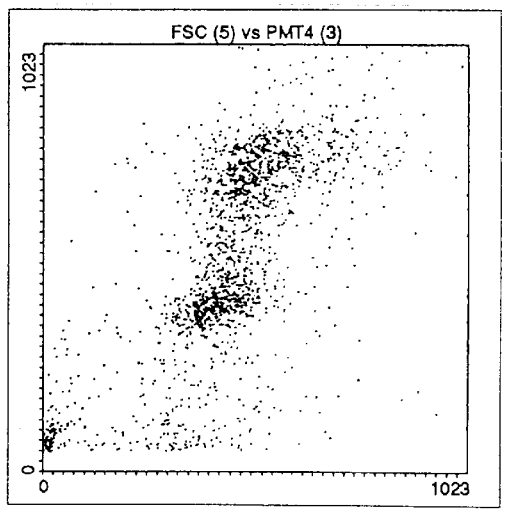
Figure 4D:
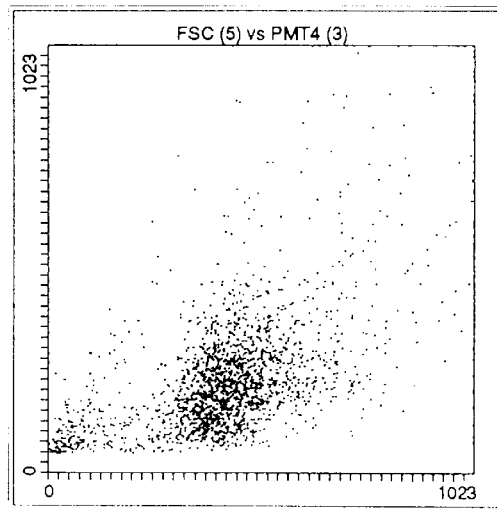

The incubated cells, including the control cells, were held for six hours and then analyzed in a flow cytometer equipped with a cell sorter (Coulter Counter ZM, Coulter Electronics, Hialeah, Fla.). The flow-cytometric analysis enabled separation of the cells according to their DNA content, and more specifically, the absolute and relative number of cells in the entire population that were in the G1 phase, the S phase, and the G2 phase. Cells in G2 phase have doubled their DNA content. FIGS. 4A–4D, which are graphs showing the number of cells plotted against the fluorescence intensity for each of the HL-60 cells treated with random oglionucleotide (FIG. 4A), irrelevant (amelogenin) ribozyme (FIG. 4B), enzymatically inactive ribozyme (FIG. 4C) and PSKH-1 RNA hammerhead ribozyme of SEQ ID NO:3 (FIG. 4D). The doubled DNA content is shown in FIGS. 4A, B and C in which the cells are divided into two populations, i.e., with and without doubled DNA content. FIG. 4D, on the other hand, shows an absence of cells in the G2 phase. The figures also show a distinct population of the cells displays a DNA content significantly below the diploid cell DNA content indicating the presence of apoptotic cells and thus the induction of the apoptotic process by ribozyme specific to PSKH-1 mRNA. Accordingly, the proper conclusion is that ribozyme specific to PSKH-1 mRNA was successful in halting or terminating cell division and growth by inactivating PSKH-1 mRNA.

The same effect, i.e., the blocking of the cell cycle, was demonstrated in HeLa-cells (ATCC CCL 2.2) with the PSKH-1 hammerhead ribozyme described in Example 4 (data not shown).

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference. PCT Application Serial No. PCT/NO96/00220 (Attorney docket no. FORSK 3.4-002), filed of even date herewith in the Norwegian Patent Office is also hereby incorporated by reference in its entirety.

Various modifications of the invention described herein will become apparent to those skilled in the art. Such modifications are intended to fall within the scope of the appending claims.

We claim:

1. A ribozyme that cleaves PSKH-1 pre-mRNA or PSKH-1 mRNA.

2. The ribozyme of claim 1, which is a hammerhead ribozyme.

3. The ribozyme of claim 2, comprising the sequence set forth as SEQ ID NO:3.

4. The ribozyme of claim 1, which is a hairpin ribozyme.

5. The ribozyme of claim 4, comprising the sequence set forth as SEQ ID NO:6.

6. A composition comprising the ribozyme of claim 1, and a carrier.

7. A composition comprising the ribozyme of claim 3 and a carrier.

8. The composition of claim 7, which is in the form of a sustained-release device.

9. The composition of claim 6, which is in the form of an aqueous composition.

* * * * *

UNITED STATES PATENT AND TRADEMARK OFFICE
CERTIFICATE OF CORRECTION

PATENT NO. : 5,856,463
DATED : January 5, 1999
INVENTOR(S) : Prydz et al.

It is certified that error appears in the above-identified patent and that said Letters Patent is hereby corrected as shown below:

On the title page, item[57]:

In the Abstract, line 5, "pre-MRNA" should read --pre-mRNA--

Column 2, line 10, "nechanisms" should read --mechanisms--.

Column 2, line 20, "CDNA" should read --cDNA--.

Column 3, line 13, after "denoted" insert --as--.

Column 9, line 41, "PSFV" should read --pSFV--.

Column 11, line 1, after "denoted" insert --in the Fig.--.

Column 11, line 2, "8" should read --3--.

Column 11, line 3, after "denoted" insert --in the Fig.--.

Column 11, line 53, after "2" insert
--and denoted as SEQ ID NO:6--

Column 11, line 55, delete "40".

UNITED STATES PATENT AND TRADEMARK OFFICE
CERTIFICATE OF CORRECTION

PATENT NO. : 5,856,463                    Page 2 of 3
DATED      : January 5, 1999
INVENTOR(S) : Prydz et al.

It is certified that error appears in the above-identified patent and that said Letters Patent is hereby corrected as shown below:

Column 12, line 4, "mNA" should read --mRNA--.

Column 12, line 62, "MRNA" should read --mRNA--

Column 13, line 20, "PSKR" should read --PSKH--.

Column 14, line 3, "CDNA" should read --cDNA--.

Column 14, line 23, "CDNA" should read --cDNA--.

Column 15, line 3, "CDNA" should read --cDNA--.

Column 15, line 4, "CDNA" should read --cDNA--.

UNITED STATES PATENT AND TRADEMARK OFFICE
CERTIFICATE OF CORRECTION

PATENT NO. : 5,856,463
DATED : January 5, 1999
INVENTOR(S) : Prydz et al.

It is certified that error appears in the above-identified patent and that said Letters Patent is hereby corrected as shown below:

Column 15, delete lines 10-12 and insert

--40.5 µl sterile $H_2O$
  5 µl 10X PCR reaction buffer
  1 µl dNTP mix (10mM each)
  0.5 µl Taq DNA polymerase (PROMEGA)(2.5 units)
  1.0 µl anchor-ligated cDNA dilution
_____
  48 µl Total Volume--

Column 15, line 46, "DATP" should read --dATP--.

Column 15, line 64, "CDNA" should read --cDNA--.

Column 15, line 64, "PSFV1" should read --pSFV1--.

Column 17, line 56, "MRNA" should read --mRNA--.

Column 30, line 7, "6" should read --7--.

Signed and Sealed this

Twentieth Day of July, 1999

Attest:

*Attesting Officer*

Q. TODD DICKINSON
*Acting Commissioner of Patents and Trademarks*